United States Patent
Mildenberger et al.

(10) Patent No.: US 6,503,496 B2
(45) Date of Patent: Jan. 7, 2003

(54) NON-ALCOHOLIC AND HYPOALLERGENIC FACE CREAM FOR THE TREATMENT OF RAZOR BUMPS

(76) Inventors: Gerard Mildenberger, 34 Atlantic Ave., Lynbrook, NY (US) 11563; Bertha Mildenberger, 34 Atlantic Ave., Lynbrook, NY (US) 11563

( * ) Notice: Subject to any disclaimer, the term of this patent is extended or adjusted under 35 U.S.C. 154(b) by 38 days.

(21) Appl. No.: 09/817,741

(22) Filed: Mar. 26, 2001

(65) Prior Publication Data

US 2001/0046480 A1 Nov. 29, 2001

Related U.S. Application Data

(60) Provisional application No. 60/195,259, filed on Apr. 7, 2000.

(51) Int. Cl.[7] .............................. A61K 7/15; A61K 7/06
(52) U.S. Cl. ........................................................ 424/73
(58) Field of Search ............................................ 424/73

(56) References Cited

U.S. PATENT DOCUMENTS 4,463,016 A * 7/1984 Mildenberger et al. ..... 424/347

* cited by examiner

Primary Examiner—James M. Spear
(74) Attorney, Agent, or Firm—Myron Amer PC

(57) ABSTRACT

Medication in liquid form for topical application in the treatment of razor bumps eschewing an alcoholic content in favor of water, glycerin, aluminum polyhydrate, propylene glycol, cellulose gum, trisodium EDTA, methylparaben, and imidazolidnyl urea, to result, upon ambient drying, into a thin film at the interface thereof with a male's shaving facial area that is 100 percent contiguous in nature so that razor bumps which occur at random locations are assured of being covered to receive the medical benefit of the medication.

1 Claim, 1 Drawing Sheet

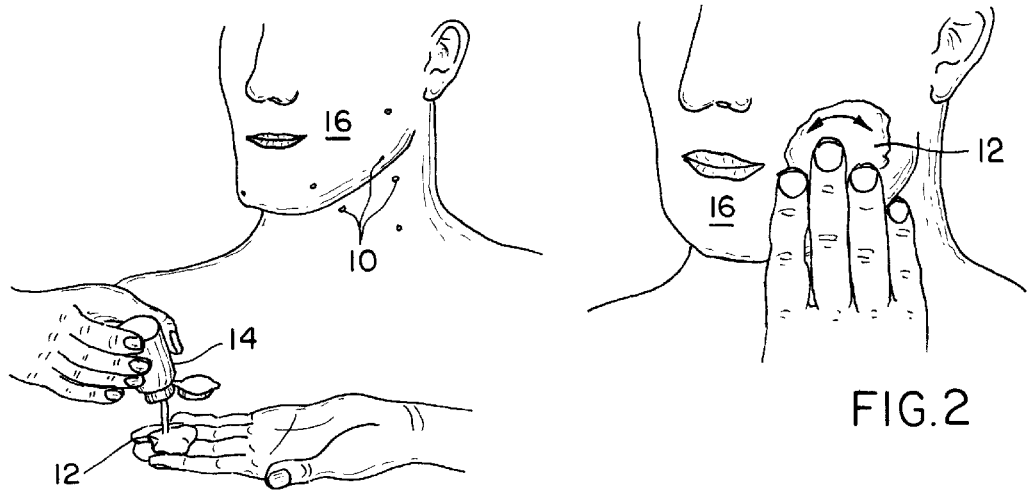
FIG.1
FIG.2
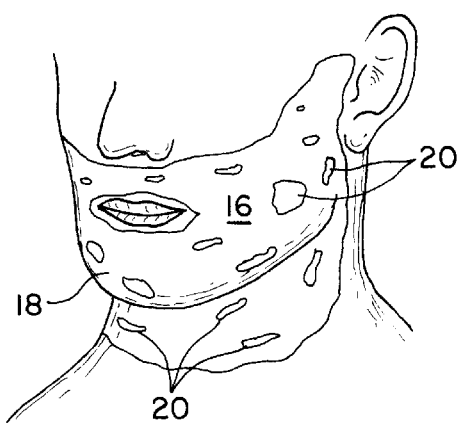
FIG.3
PRIOR ART
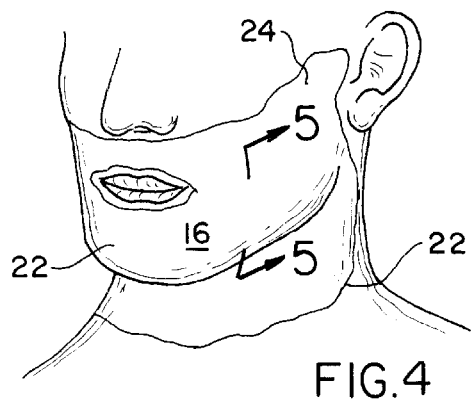
FIG.4
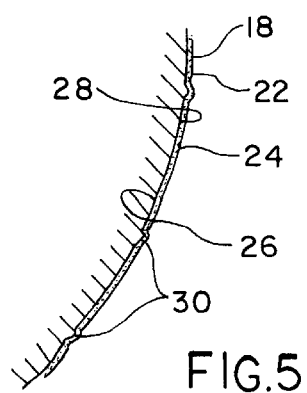
FIG.5

NON-ALCOHOLIC AND HYPOALLERGENIC FACE CREAM FOR THE TREATMENT OF RAZOR BUMPS

CROSS REFERENCE TO RELATED APPLICATIONS

This application claims the benefit of United States Provisional Patent Application No. 60/195,259, filed on Apr. 7, 2000, the contents of which are incorporated herein by reference thereto.

The present invention relates generally to improved topical application of hypoallergenic face cream for the treatment of razor bumps in which, more particularly, the face cream that is topically facially applied is characterized by also being non-alcoholic which significantly contributes to its effectiveness for the end purposes intended.

BACKGROUND OF THE INVENTION

Pscudofoillculids of the beard, commonly known as razor bumps, is an inflammatory state of the neck and chin which is characterized by trythematous lesions, firm papules and pustules containing buried hairs. Observation and examination indicates that razor bumps are the result of a facial hair growing from a follicle and undergoing a reverse change in curvature so that the free end projects into the skin through an unoccupied adjacent pore. This occurrence is akin to what is commonly referred to as an ingrown hair. At the skin-piercing opening in the skin by the free end of the hair, by natural occurrence, the above noted inflammation and infection results.

There are today numerous commercially available face creams and gels which are formulated to cure entirely or at the least significantly obviate the occurrence of razor bumps. In all of these commercially available face creams and gels there is used in the formulation, to a significant extent, the ingredients of alcohol and/or aspirin, both primarily to reduce inflammation and infection. Exemplary of one such commercially available face cream is the article of manufacture of U.S. Pat. No. 4,463,016 for "Method For the Treatment of Razor Bumps" issued to Burgess on Jul. 31, 1984 chemically constituented, at least in part, with cetyl alcohol as a combining vehicle with the inflammation and infection-reducing content thereof to facilitate topical application.

BRIEF SUMMARY OF THE INVENTION

In contrast to the aforesaid and all other known commercially available products, the within inventive face cream and gel is formulated totally without use of alcohol or aspirin. The consequence of eliminating aspirin is a significant development because it causes, in many individuals, an allergic reaction. A similar point of utility is achieved in the elimination of alcohol since the resulting formulation permits its use in penal institutions and other sites of use where the inventive product can be diluted into a fluid and, if it contained alcohol, could then be misused as a potable liquid.

As a substitute for alcohol and aspirin, the within inventive face cream has as a major ingredient a chemical consisting of aluminum polyhydrate. In use, aluminum polyhydrate applied topically is effective to infuse oxygen into and below the skin and this in turn will result in diminishing the inflammation of the razor bumps. For this unusual operating mode the manufacture of the aluminum polyhydrate is carried out under conditions resulting in super saturation of oxygen which, in a desaturation process contributes to a desirable high volume of oxygen which, as already noted, will infuse into and below the skin and result in diminishment of the inflammation and infection.

Underlying the present invention is the recognition that alcohol, when used in the vehicle supposedly to facilitate the topical facial application, is actually counterproductive to this end because of its evaporative nature, thus leaving areas of the topical facial application without inflammation and infection-reducing medication. Since the razor bumps occur at random locations, there is therefor location occurrences at which no inflammation and infection treatment is taking place according to prior art practice.

Broadly, it is an object of the present invention to provide topical facial application of razor bump face cream overcoming the foregoing and other shortcomings of the prior art.

More particularly, it is an object to eschew the use of alcohol content in a razor bump-treatment face cream so that the face-covering film formed by ambient drying of the face cream is characterized by being in 100 percent contiguous relation at the interface of the film and facial areas, thereby obviating any locations at which no inflammation and infection treatment is taking place, as now occurs according to prior art practice.

BRIEF DESCRIPTION OF THE SEVERAL VIEWS OF THE DRAWING

The description of the invention which follows, together with the accompanying drawings should not be construed as limiting the invention to the example shown and described, because those skilled in the art to which this invention appertains will be able to devise other forms thereof within the ambit of the appended claims.

FIGS. 1 and 2 are perspective views illustrating, in sequence, the topical application of razor bump face cream;

FIG. 3 illustrates a prior art non-contiguous ambient-dried film of a topically applied razor bump face cream of prior art chemically constituented content;

FIG. 4 is a view similar to FIG. 3, but illustrating a contiguous ambient-dried film of a topically applied razor bump face cream chemically constituented without alcohol content according to the present invention; and FIG. 5 is a cross-sectional view of the film of FIG. 4 as taken along line 5—5 of FIG. 4.

DETAILED DESCRIPTION OF THE INVENTION

The treatment of razor bumps, individually and collectively designated 10 occurring at random locations coincident with the correspondingly random occurrence of below skin surface inflammation and infection contemplates the topical application of face cream 12 from a commercially purchased bottle 14 spread over the entire face area 16, where an inflicted individual experiences beard growth. Ambient drying of the thusly applied face cream 12 results, when the face cream uses alcohol, such as cetyl alcohol, or a chemical alcohol equivalent, in a non-contiguous dried film 18 having unoccupied areas, individually and collectively designated 20, in which, more particularly, what is not present in the areas 20 is inflammation and infection-reducing medication, it having been determined by observation that such areas 20 exist and it being believed that their existence is caused by either the removal by, or the failure to remain, of the inflammation and infection-reducing medication as a result of the evaporation of the alcohol content of a chemically constituented prior art face cream 12.

As a significant improvement, and as shown in FIGS. 4 and 5, is topically applied face cream 22 which it will be understood is chemically constituented without alcohol, or aspirin, content and which, as a result, particularly as a consequence of non-use of alcohol or its chemical equivalent, produces after ambient drying a thin 100 percent contiguous film 24 having surface-to-surface contact, as at 26, at the interface of the film 18 and facial area 28. The contact 26 at the interface 18, 28 is maintained for a selected time duration of hours, usually from a morning application to a next day morning application, before a dried film 24 is removed by being washed off preparatory to replacement with another topical application. In practice, it has been found that in the allotted time interval, the face cream 22 is more effective. It is believed the contiguous nature of its dried film 24 contributes to providing a more effective inflammation and infection-reducing consequence to the inflicted individual's razor bumps 30.

For completeness sake, there is set forth below, in separate paragraphs, a list and description of the preferred embodiment of an exemplary formulation of the within inventive face cream and gel 22:

Aluminium Polyhydrate—(Gloss White) Usually obtained as a white, bulky, amorphous powder. Practically insoluble in water but soluble in alkaline solution. Used as an absorbent, emulsifier, and alkali in detergents, antiperspirants, and dentifrices. Used medicinally as a gastric antacid. No known toxicity;

Glycerine (Glycerol)—Any by-product of soap, it is a sweet, warm-tasting, oily fluid obtained by adding alkalies to fats and fixed oils. A solvent, humectant, and emollient in many cosmetics, it absorbs moisture from the air and, therefore, helps keep moisture in creams and other products to spread better. Among the many products containing glycerin are cream rouges, face masks, and freckle lotion, mouthwashes, skin fresheners and toothpaste;

Propylene Glycol—One of the most widely used cosmetic ingredients, it is a clear, colorless, viscous liquid, slightly bitter tasting. Used in liquid makeup, spray deodorants, hair straighteners and baby lotions;

Cellulose Gums—Any of several fibrous substances consisting of the chief part of the cell walls of plants. They are used as emulsifiers and hand creams and lotions. They are resistant to bacterial decomposition and give uniform viscosity to products. No known toxicity;

Trisodium EDTA—Powdered sodium salt that reacts with metals. Can deplete the body of calcium if taken internally. No known toxicity on the skin;

Menthylparaben—Used in bubble baths, cold creams, eyeliners, and liquid makeup. It is an anti-microbial and preservative made of small, odorless, colorless crystals that have a burning taste. Nontoxic in small amounts; and Imidazolidinyl Urea—The most commonly used cosmetic preservative after the parabens, it is the second most identified cosmetic preservative causing contact dermatitis, according to the American Academy Dermatology Standard on vehicle and preservative Patch Testing Tray results. It is colorless, odorless, and tasteless and is employed in baby shampoos, lotions, eye shadows, colognes, powders and moisturizers. No known toxicity.

While the topical application of the razor bump face cream disclosed in detail is fully capable of attaining the objects and providing the advantages hereinbefore stated, it is to be understood that it is merely illustrative of the presently preferred embodiment of the invention and that no limitations are intended to the detail of construction or design herein shown other than as defined in the appended claims.

What is claimed is:

1. A method of treating razor bumps and skin inflammation on the facial areas shaved by a male with an alcohol free composition comprised of water, glycerin, aluminum polyhydrate, propylene glycol, cellulose gum, trisodium EDTA, methylparaben and imidazolidinyl urea wherein said method comprises the steps of:

(1) applying said composition in covering relation over said facial areas in which said razor bumps and skin inflammation occur in random locations;

(2) forming by ambient drying of said applied composition a thin film as results from said composition characterized by a 100 percent contiguous relation at an interface of said thin film and facial areas; and (3) maintaining intact said 100 percent contiguous relation of said interface for a select time duration of hours before attempted manual removal of said thin film;

whereby during said time duration of hours said 100 percent contiguous relation of said thin film assures treatment of all razor bumps and skin inflammation in said random locations.

\* \* \* \* \*